United States Patent [19]
Mirza

[11] Patent Number: 5,928,239
[45] Date of Patent: Jul. 27, 1999

[54] PERCUTANEOUS SURGICAL CAVITATION DEVICE AND METHOD

[75] Inventor: Sohail K. Mirza, Bellevue, Wash.

[73] Assignee: University of Washington, Seattle, Wash.

[21] Appl. No.: 09/039,736

[22] Filed: Mar. 16, 1998

[51] Int. Cl.⁶ ................................................. A61B 17/32
[52] U.S. Cl. ............................ 606/79; 606/83; 606/167
[58] Field of Search ................................ 606/80, 79, 81, 606/83, 84, 86, 167, 170, 171, 180

[56] References Cited

U.S. PATENT DOCUMENTS

| | | | |
|---|---|---|---|
| Re. 33,258 | 7/1990 | Onik et al. ............................... | 604/22 |
| 4,596,243 | 6/1986 | Bray ......................................... | 128/92 |
| 4,961,740 | 10/1990 | Ray et al. ................................. | 606/61 |
| 5,015,255 | 5/1991 | Kuslich ..................................... | 623/17 |
| 5,026,373 | 6/1991 | Ray et al. ................................. | 606/61 |
| 5,041,119 | 8/1991 | Frigg wt al. ............................. | 606/96 |
| 5,055,104 | 10/1991 | Ray ........................................... | 606/61 |
| 5,059,193 | 10/1991 | Kuslich ..................................... | 606/61 |
| 5,062,845 | 11/1991 | Kuslich et al. .......................... | 606/80 |
| 5,263,953 | 11/1993 | Bagby ....................................... | 606/61 |
| 5,431,671 | 7/1995 | Nallakrishnam ........................ | 606/167 |
| 5,445,639 | 8/1995 | Kuslich et al. .......................... | 606/80 |
| 5,489,307 | 2/1996 | Kuslich et al. .......................... | 623/17 |
| 5,489,308 | 2/1996 | Kuslich et al. .......................... | 623/17 |
| 5,609,636 | 3/1997 | Kohrs et al. ............................. | 623/17 |
| 5,658,337 | 8/1997 | Kohrs et al. ............................. | 623/17 |
| 5,693,011 | 12/1997 | Onik ......................................... | 604/22 |
| 5,700,291 | 12/1997 | Kuslich et al. .......................... | 623/17 |
| 5,709,683 | 1/1998 | Bagby ....................................... | 606/61 |
| 5,720,748 | 2/1998 | Kuslich et al. .......................... | 606/80 |

*Primary Examiner*—Michael Buiz
*Assistant Examiner*—Shai Daphna
*Attorney, Agent, or Firm*—Delbert J. Barnard

[57] ABSTRACT

A device and method for percutaneous surgical cavitation. The device includes an elongated shaft and cutting tip interconnected by a freely-rotating hinge. Upon rotation of the shaft to a sufficient velocity, the cutting tip will be deflected toward a position that is angularly offset from the shaft's access of rotation. The length of the cutting tip will determine the radius of the cavity being formed, which may be several times the radius of the shaft. The method of the present invention provides for formation of a cavity within a body through a small percutaneous access opening such that an enlarged cavity may be formed without an invasive access opening. The present invention also provides a method of percutaneous prophylactic replacement of osteoporotic bone wherein weakened bone material is removed from a cavity using only a needle-sized access opening. Strengthening bone replacement material, such as bone cement, can be injected into the cavity to provide reinforcement of weakened bone without invasive surgical access.

18 Claims, 10 Drawing Sheets

FIG. 27 ent vertebral bodies between which a substantially hemi-

PERCUTANEOUS SURGICAL CAVITATION DEVICE AND METHOD

TECHNICAL FIELD

This invention relates to a device and method of forming a cavity in soft tissue or bone in a minimally invasive manner. Specifically, it relates to a device that may be inserted percutaneously, such as through a needle or cannula and then expanded in diameter upon rotation to form an internal cavity having a radius many times that of the insertion opening.

BACKGROUND INFORMATION

Minimizing harm to patients during medical treatment has been a guiding principle of physicians since the days of Hippocrates. For surgeons, this principle has meant minimizing the surgical injury to the patient while at the same time achieving the goals of the surgical procedure. Some practical applications of this principle have achieved new levels of success with the technological advancements of minimally invasive surgery. Techniques using indirect and direct visualization methods allow performance of surgical work through small openings. These techniques have been refined to successful clinical applications, particularly over the past ten years. Orthopedic, gynecologic, and thoracoabdominal surgical techniques have been revolutionized by progress in minimally invasive surgical techniques. Minimally invasive techniques are also used in neurosurgical procedures to minimize surgical injury to critical neural tissues. Additionally, techniques have been developed to allow percutaneous removal of intervertebral discs.

A device for forming an intervertebral cavity having a radius greater than that of the entry opening is shown in U.S. Pat. No. 5,062,845 and 5,445,639.

SUMMARY OF THE INVENTION

The present invention provides a device for percutaneous surgical cavitation comprising an elongated shaft and a fixed length cutting tip interconnected by a hinge. The hinge allows angular deflection of the cutting tip relative to the elongated shaft when the device is rotated at sufficient velocity.

It is an object of the present invention to provide a device that is capable of forming an enlarged cavity having a radius greater than that of the percutaneous access opening.

According to one method of the present invention, percutaneous formation of a cavity within a body comprises the steps of providing a percutaneous access opening, inserting a device constructed according to the present invention, rotating the device at a velocity sufficient to cause the cutting tip to be deflected away from an access of rotation of the device, and withdrawal of the device through the percutaneous access opening which has a radius smaller than that of the formed cavity.

According to other aspects of the method, the device can be axially advanced or withdrawn to enlarge the length of the cavity, multiple interconnecting cavities can be formed, ablated material can be removed by irrigation and suction, and replacement material can be injected into the cavity through the percutaneous access opening.

The present invention also provides a method of percutaneous prophylactic replacement of osteoporotic bone in which a cavity is formed in the weakened bone and replaced with a material of increased strength through the percutaneous access and without invasive open surgery.

BRIEF DESCRIPTION OF THE DRAWINGS

Like reference numerals are used to indicate like parts throughout the various figures of the drawing, wherein.

BEST MODE FOR CARRYING OUT THE INVENTION

The device and method of the present invention are particularly suited to three distinct purposes. The first is strengthening of weakened bone tissue. The primary application of this purpose is to prevent fractures of the hip (neck of the proximal femur). Secondarily, it may be applied to a surgical procedure of the spine to reduce or eliminate back pain caused by trauma or degenerative disease. Additionally, it may be used for the prevention or treatment of distal radius (wrist) or proximal humerus (shoulder) fractures.

The second primary application of the device and method of the present invention is for ablation of cystic lesions of bone (tumors) or in soft tissue (intracranial brain tumors). The third principle application of the present invention is for intervertebral or sacroiliac joint fusion to reduce or eliminate back pain.

Osteoporosis is the most common problem in patients with musculoskeletal disorders. Fractures from osteoporosis occur in load-bearing regions of the skeleton with large volumes of soft, spongy, cancellous bone. These regions are the metaphyseal areas of long bones such as the radius, femur, humerus, and the central portion of vertebral bodies. This invention may allow prevention of some of the devastating consequences of osteoporosis-related bone fractures.

Osteoporosis decreases the bone's load-bearing capacity. This weakening of bone leads to an increased susceptibility to fracture. With advanced osteoporosis, even physiologic loads from routine every day activities can result in fractures. The most common fracture sites are spine, wrist and hip. In many cases, a hip fracture is not the result of a fall, but rather the fall is the result of a hip fracture caused merely by standing or walking. The population at risk for these fractures has been identified by large-scale epidemiologic studies. This at-risk population is increasing in number as the "baby boomer" generation ages. Also, increased life expectancy is increasing the percentage of older adults in the total population. Furthermore, these older adults are pursuing more active lifestyles. These lifestyles are increasingly limited by osteoporosis. Other patients at risk for osteoporosis and its complications are transplant recipients and patients with inflammatory disorders requiring long-term steroid use. Patients with chronic conditions requiring ongoing medication, such as anti-epileptic drugs, are also at risk for osteoporosis-related fractures.

Pathologic lesions from metastatic disease also weaken the bone's ability to resist normal loads. These lesions could be stabilized with a minimally invasive cavitation device. The device would destroy the tumored tissue, permitting evacuation of the liquefied tumor tissue with irrigation and suction. The cavity could either be filled with injectable graft materials or bone graft substitutes, such as surgical bone cement. Prophylactic fixation of these lesions could potentially avoid fractures and prevent associated morbidity. Hemostatic, chemotherapeutic and anti-bacterial materials may be included with the injectable graft material. Bioabsorbable compounds are ideally suited for prophylactically reinforcing the weakened bone. Hydroxyapatite-related compounds could avoid potential implant related problems. Methylmethacrylate could also be used. Antibiotic impregnation of the graft material could further decrease the potential risk of infection.

Prophylactic fixation of osteoporotic bone is not currently in use due to the surgical morbidity associated with invasive fixation procedures. To be effective and practical, a prophylactic fixation procedure must be minimally invasive and carry very low risk of procedure-related complications. Previously, no methods existed for percutaneous prophylactic fixation of weakened osteoporotic bone. Existing methods require general anesthia, large incisions, blood loss and are associated with long recovery periods and post-operative pain. These concerns limit the ability of prophylactic fixation of weakened bones in patients who have osteoporosis, since they are generally elderly patients with other significant co-existing medical conditions that place them at a higher risk for anesthesia and post-operative complications. The risk/benefit scale could shift dramatically if these surgical concerns are diminished. The ability to perform such a procedure percutaneously would allow the use of local anesthesia and operation on an out-patient basis.

The cavitation tool of the present invention may be inserted percutaneously to allow reinforcement of bone in critical areas without invasive open surgery. In most cases, a local anesthetic could be used. Without the need for general anesthesia, anesthesia-related complications could be avoided. Minimal incisions would decrease post-operative pain and the risk of infection.

The device and method of the present invention could also be used for joint arthrodeses (fusions). Previously, joint fusions were performed through open approaches. Occasionally, arthroscopic techniques are used. For intervertebral fusion in the spine, current and previous techniques have employed laparoscopic surgery. These techniques still require admission to a standard operating room and general anesthesia. The cavitation tool of the present invention will allow percutaneous fusion to be performed under local anesthesia as an out-patient procedure.

Use of bioabsorbable materials to fill the formed cavity would avoid potential implant-related complications. The absorbable graft material could be replaced by the body over time with bone, thereby eliminating foreign material. Bone graft substitutes are currently available which closely replicate the natural mineral content of bone and are, therefore, much more friendly to local host tissues.

Referring to the various figures of the drawing, and first to FIGS. 1–7, thereon is shown at 10 a passively-hinged cavitation tool according to a preferred embodiment of the present invention. The device includes a substantially cylindrical shaft 12 with a freely hinged cutting tip 14 at its most distal end. The shaft 12 and cutting tip 14 are interconnected by a single axis hinge 16.

In preferred form, the shaft 12 and cutting tip 14 are both made from like material. The hardness and exact nature of this material will be determined by the particular tissue into which a surgical cavity is to be formed. Typically, the device is made entirely of stainless steel or titanium. Cavitation in hard bone will require the use of harder, heavier or stiffer material than that required for cavitation in soft tissue such as brain or liver.

A diametrical slot 18 is formed across the distal end of the shaft 12. A peninsular tang is formed at the proximal end of the cutting tip 14. This tang 20 is sized to provide adequate clearance in the transverse slot 18 such that the cutting tip 14 will be freely pivotable relative to the shaft 12. A diametrically transverse hold perpendicular to the slot 18 is formed through the distal end of the shaft 12 and tang portion 20 of the cutting tip 14. The hole though the tang portion 20 may be slightly enlarged relative to the hole through the clevis ears on each side of the slot 18. In this manner, a hinge pin 22 can be selected having a diameter which is snuggly received within the holes in the distal portion of the shaft 12 and freely received through the hole in the tang portion 20 of the cutting tip 14.

Additionally, the distal end portion 24 of the shaft 12 and proximal end 26 of the tang portion should be rounded so as to prevent interference between the shaft 12 and cutting tip 14 as the tip is pivoted to an angular or perpendicular orientation.

Figure 1:
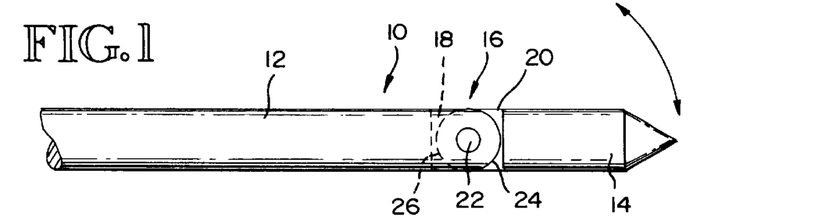
FIG. 1 is a plan view of the distal portion of a percutaneous surgical cavitation device according to a preferred embodiment of the present invention.
Figure 2:
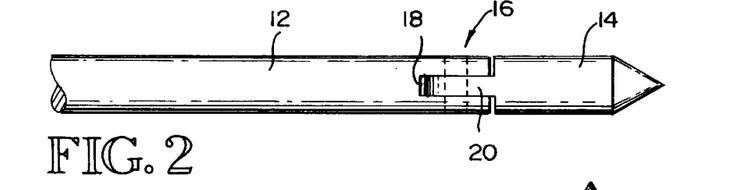
FIG. 2 is a top view thereof.
Figure 3:
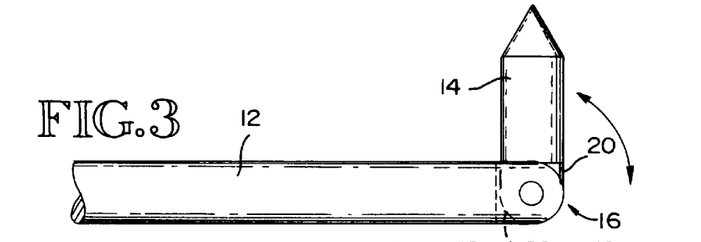
FIG. 3 is a view similar to FIG. 1 but in which a freely-rotatable tip portion has been swung 90° relative to an axis of rotation for the shaft.
Figure 4:
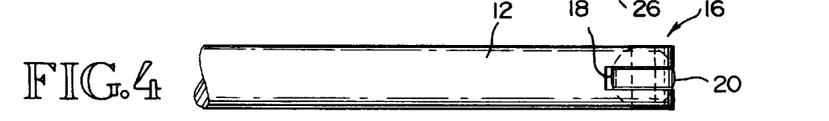
FIG. 4 is a bottom view thereof.
Figure 5:
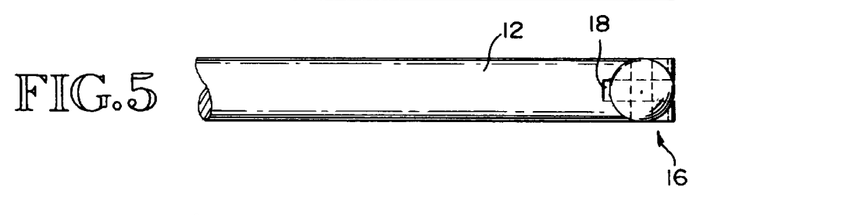
FIG. 5 is a top view thereof.
Figure 6:
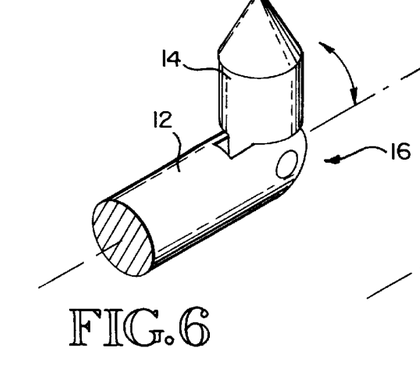
FIG. 6 is a pictorial view similar to that shown in FIGS. 3–5.
Figure 7:
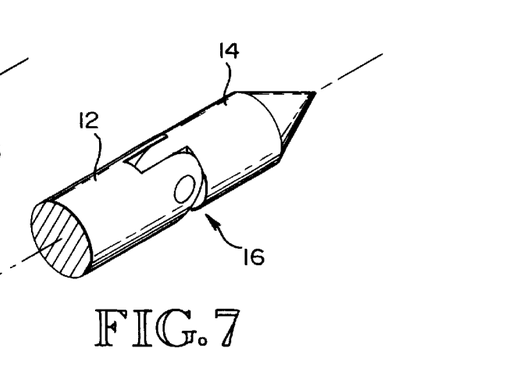
FIG. 7 is a pictorial view similar to that shown in FIGS. 1 and 2.
Figure 8:
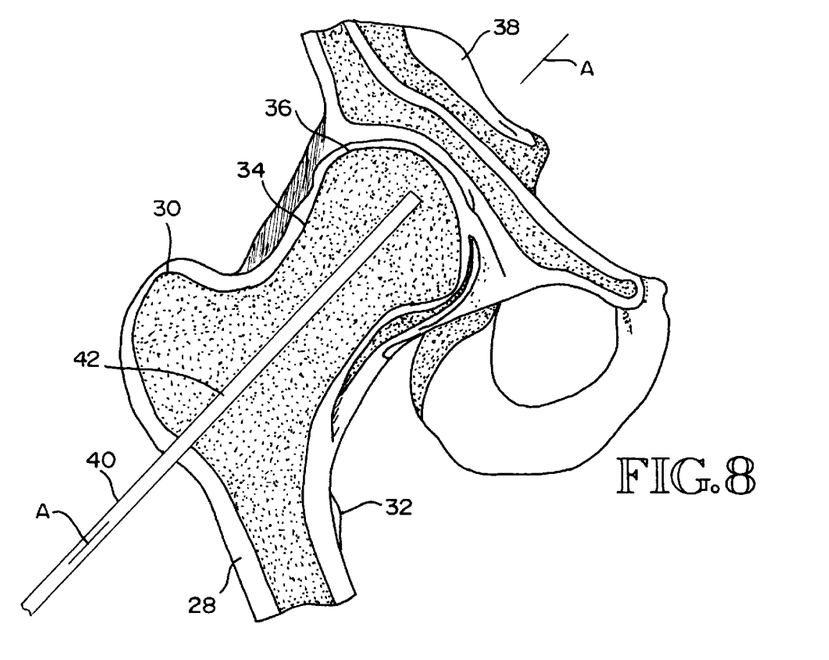
FIGS. 8–16 are coronal (frontal) sectional views through a human right hip joint showing subsequent steps for replacement of disease-affected bone tissue with graft material or bone graft substitutes for prophylactic fixation of weakened osteoporolic bone in the proximal femur.

Referring now to FIGS. 8–16, and first to FIG. 8, therein is shown a coronal (frontal) sectional view through a human right hip joint. A proximal portion of the right femur 28 is shown including, for reference, the greater trochanter 30, the lesser trochanter 32, the neck 34, and head 36 portions. Also shown in partial section is the ilium 38.

An expected use of the device and method of the present invention is to facilitate percutaneous prophylactic fixation of an osteoporotic proximal femur to reduce risk of fracture. Previous methods of fixation required invasive open surgery and installation of a metal screw or pin. Because of the surgical risks involved, such a procedure has not been performed prophylactically, but is limited to post-traumatic situations. According to the present invention, a guide 40 or other guide cannula is inserted percutaneously through soft tissue into contact with the proximal femur 28. The guide 40 is aligned according to a predetermined axis A—A. This axis is determined according to preoperative imaging or active fluoroscopy during the procedure. A drill is inserted through the guide 40 and a pilot hole 42 is formed with an ordinary orthopedic drill according to well-known procedures. The depth of this pilot hole 42 is determined preoperatively and is formed co-axial with the predetermined axis A. The diameter of the pilot hole 42 corresponds with the diameter of the cavitation tool shank 12. This is typically in the range of about 3.0 to 5.0 mm, although it is to be understood that variations both larger and smaller are envisioned within the scope of this invention.

Figure 9:
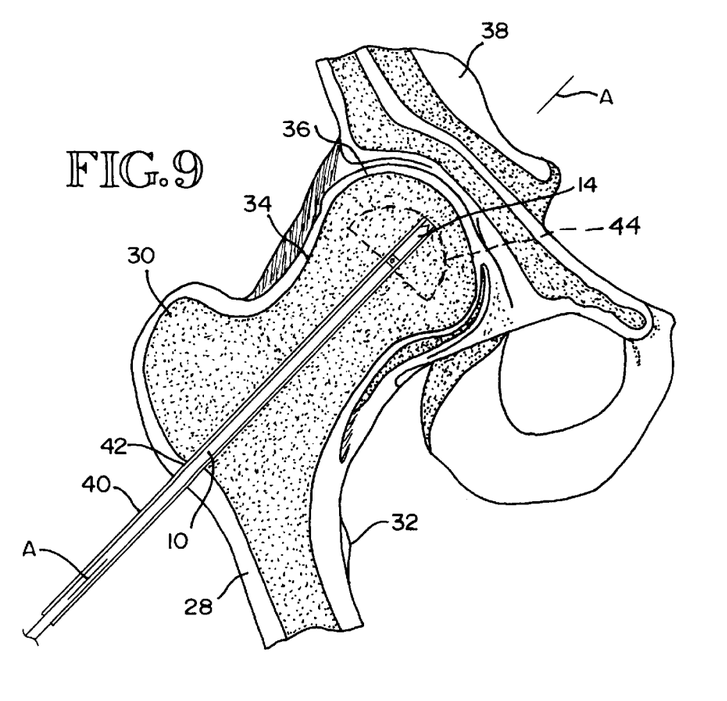

Referring now to FIG. 9, a cavitation-forming device 10 according to the present invention is inserted through the guide 40 and pilot hole 42. The length of the tip portion 12 determines the size of a first semi-spherical cavity 44 to be formed.

Figure 10:
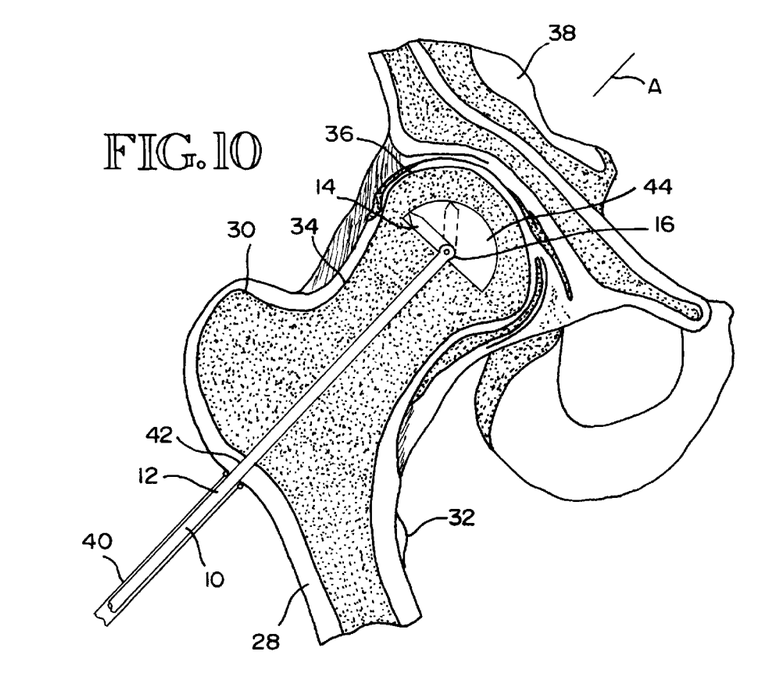

Referring now to FIG. 10, the shaft 12 of the cavitation device 10 is then operated to rotate at high speed. In preferred form, this is in the range of 40,000 to 80,000 rpm. Rotational power for driving the device 10 may be supplied by any of a number of known and widely-available devices.

Figure 11:
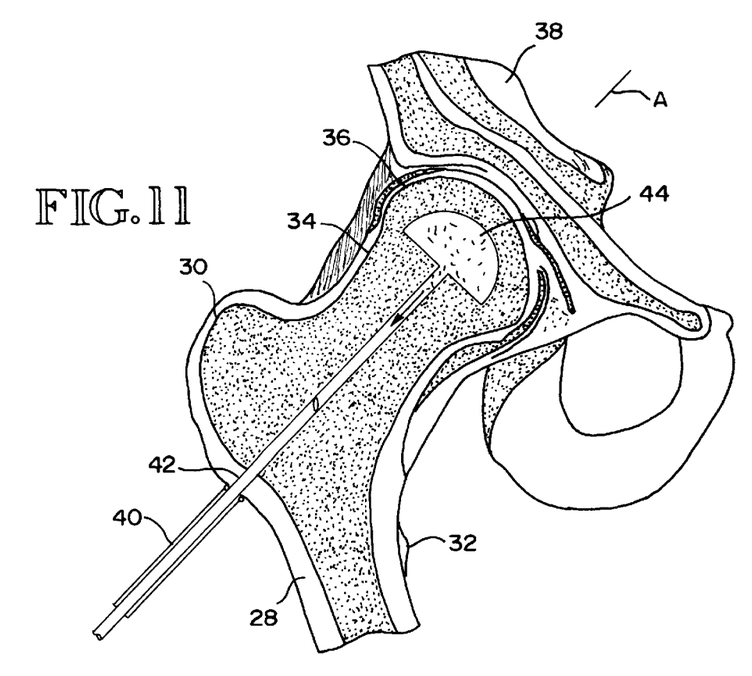

The rotational velocity imparted on the shaft 12 will initially be imparted also onto the cutting tip portion 14. Initially, this is in the form of axial rotation aligned with axis A. The rotational velocity transferred to the cutting tip 14 results in a centrifugal force (or more specifically, lack of centrifugal pull) causing the cutting tip 14 to begin to angle at the pivot hinge 16. At first, this will result in the cutting tip 14 (shown in phantom line) to be swung in a substantially conical configuration. Ultimately, the cutting time 14 moves to a perpendicular orientation, unless otherwise restrained against such movement. It is expected that rotation at 80,000 rpm for no more than 10 seconds will be sufficient to liquefy the bone material in the path of the cutting tip 14 resulting in a substantially semi-spherical cavity 44. Referring now to FIG. 11, thereafter, the device 10 can be withdrawn and the liquefied material can be evacuated by use of well-known irrigation and suction techniques. Following this step, a hemostatic agent or balloon tamponade may be used to control internal bleeding. If deemed necessary, other agents, such as antibiotics or anesthetics, may be introduced at this time.

It can be noted from FIG. 11 that a "safe zone" is maintained around the periphery of the semi-spherical cavity 44 and between the outer surface of the femur's head portion 36. The maintaining of this "safe zone" will determine the maximum radius of the cavity 44 and, in turn, the maximum length of the cutter tip 14.

Figure 12:
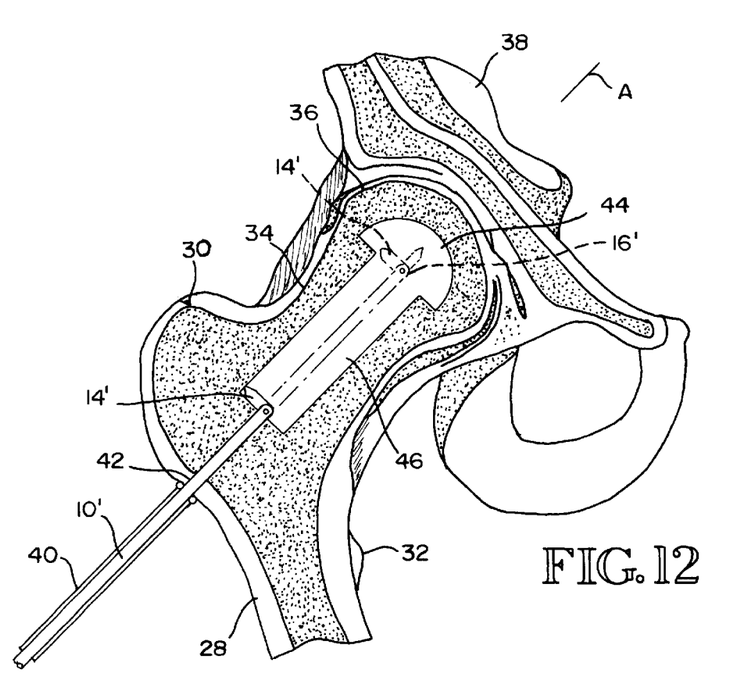

Referring now to FIG. 12, thereafter, another cavitation device 10' is inserted through the guide 40. The length of cutting tip 14' is selected to correspond with the desired radius of a neck cavity 46 to be formed co-extensive with axis A. This cavity 46 is formed by inserting the cavitation device 10' until the hinge portion 16' extends just into the semi-spherical cavity 44. The device 10' is then rotated at a predetermined velocity and withdrawn slowly along axis A, guided by the pilot hole 42 and guide 40 to form the substantially-cylindrical neck cavity 46.

Figure 13:
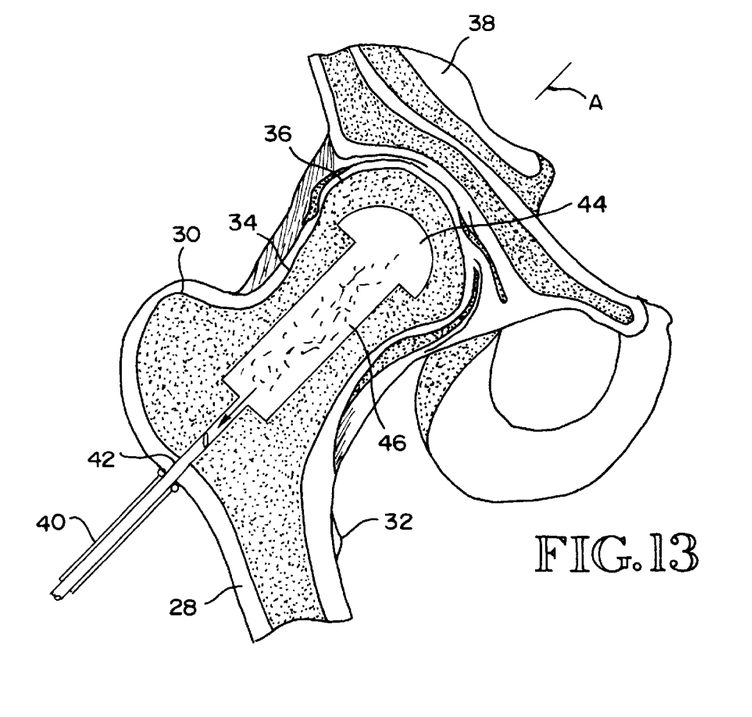

Referring now to FIG. 13, the liquefied bone material is then evacuated through well-known irrigation and suction techniques. As described above, steps may be taken as necessary to control bleeding, infection or pain. Likewise, an expandable balloon filled with contrast medium may be inserted into the cavities 44, 46 in order to make a confirmational image.

Figure 14:
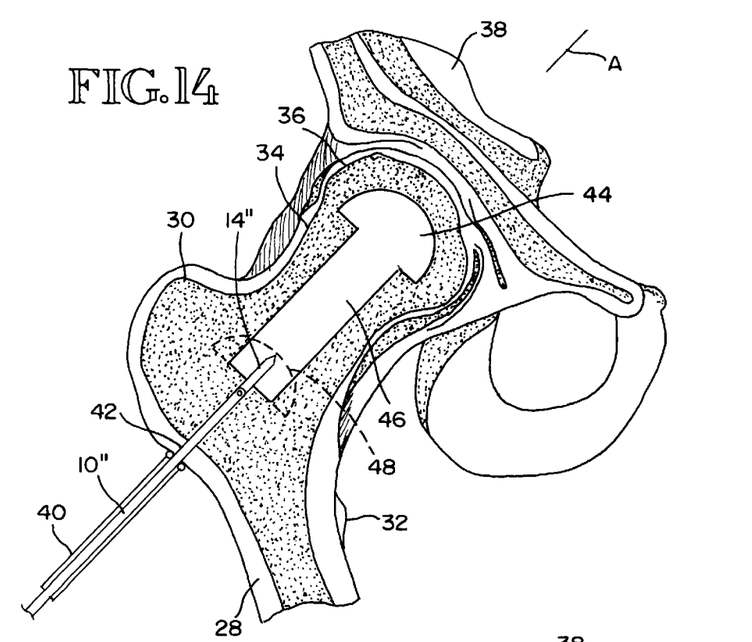
Figure 15:
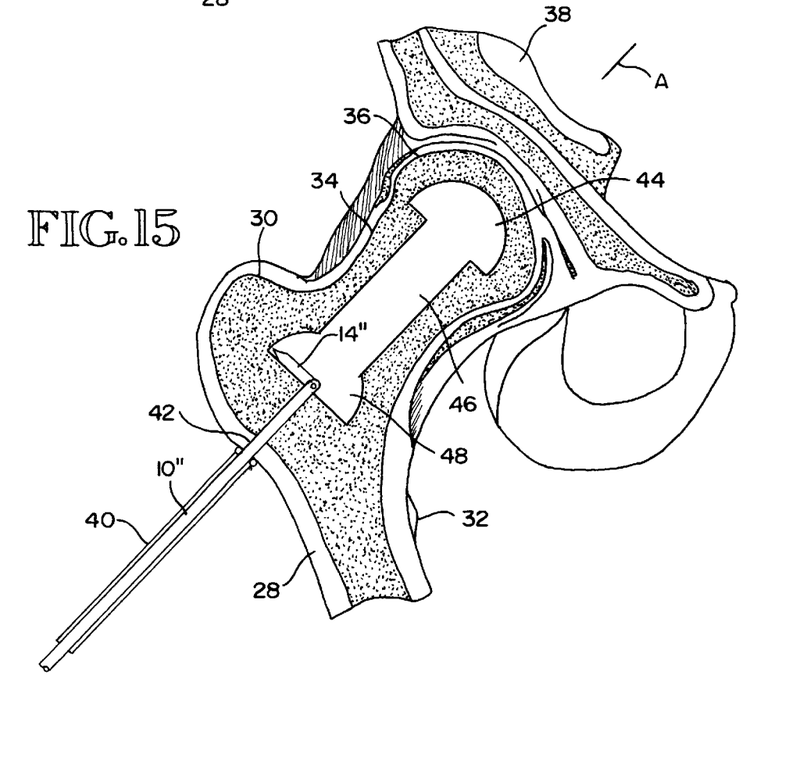

Referring now to FIG. 14, an enlarged third cavity 48 may be formed using yet another cavitation device 10" having a tip portion 14" of predetermined length to correspond with the desired radius of the cavity 48. The axis of rotation of the cavitation device 10", as well as the axis of the guide, are maintained co-extensive with axis A. The cutting device 10" is positioned at a depth to correspond with the predetermined location of the third cavity 48. This may or may not overlap part of the cavity 46 that was previously formed. As shown in FIG. 15, the radius of this third cavity 48, which corresponds approximately with the greater trochanter 30, may be equal to or greater than that of the head portion cavity 44. Similar evacuation, hemostatic, antibiotic and anesthetic techniques may again be employed. If it is desired to again image the composite of the cavities 44, 46, 48, a balloon filled with contrast medium may be inserted.

Once the desired cavity is formed, the ultimate step of the prophylactic fixation technique is to fill the cavity with a stronger material, such as bone cement, to reinforce the neck and head portions 34, 36 of the proximal end of the femur 28.

Figure 16:
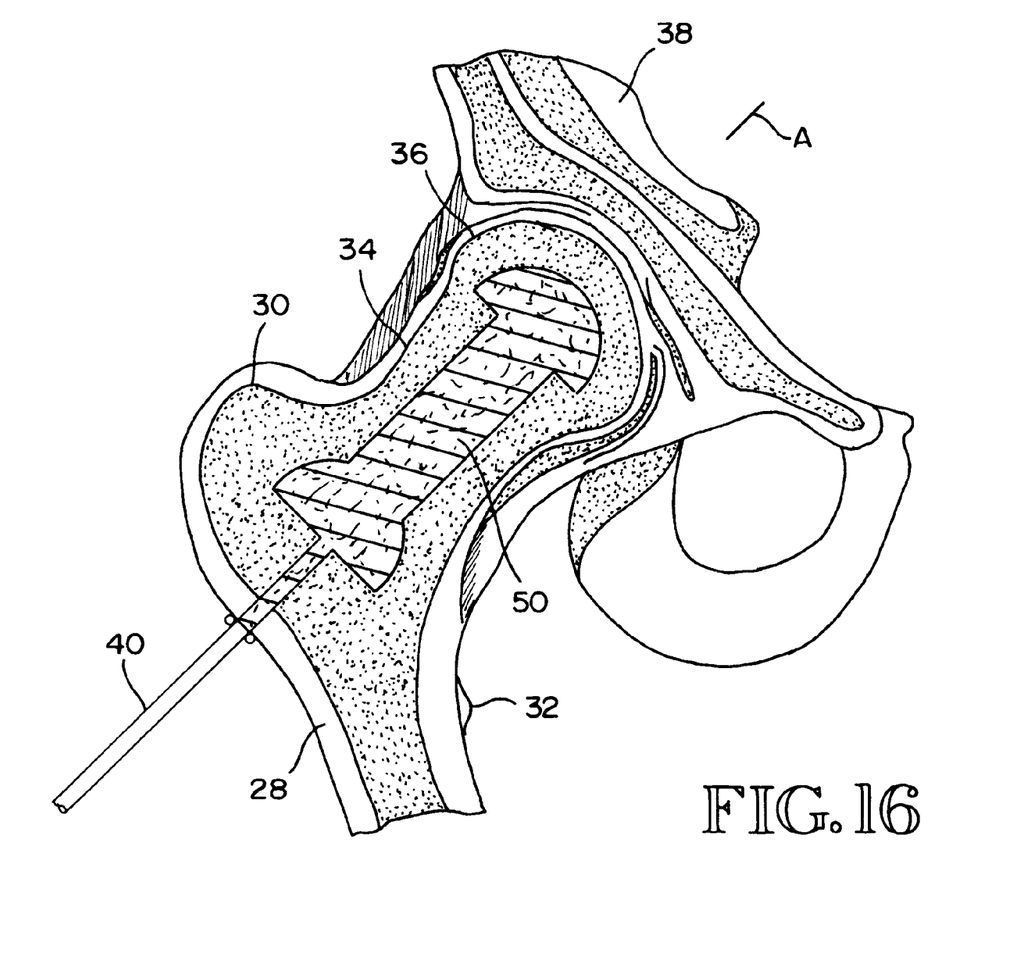
Figure 17:
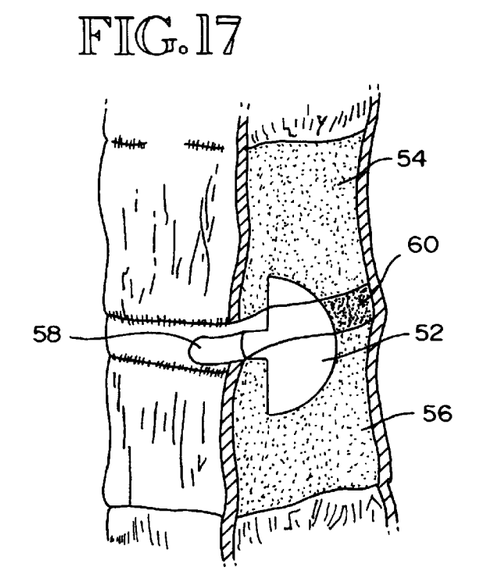
FIG. 17 shows a sagittal/coronal sectional view of adjacent vertebral bodies between which a substantially hemispherical cavity has been formed according to the present invention.
Figure 18:
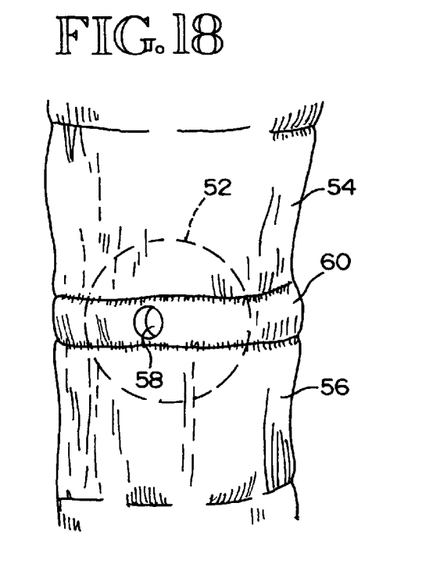
FIG. 18 shows a similar, non-sectioned view indicating the relative location of the entrance opening and internal enlarged cavity.
Figure 19:
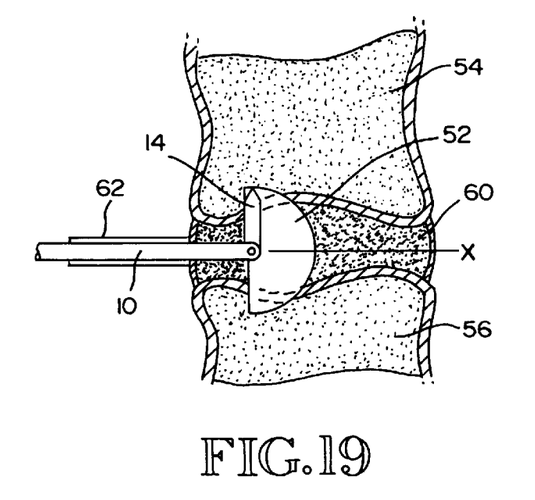
FIGS. 19 and 20 show the formation of an intervertebral cavity formed according to the present invention in which a portion of the intervertebral disc and portions of the adjacent vertebral bodies have been removed.
Figure 20:
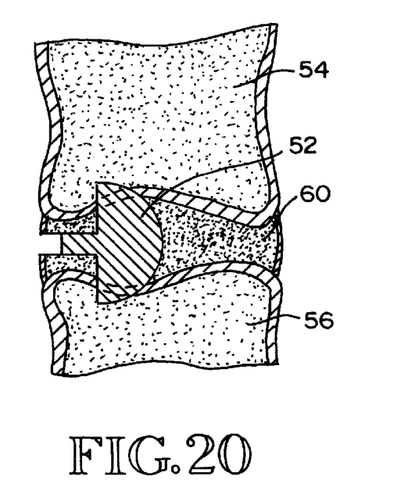

Referring to FIG. 16, the bone cement forms a plug 50 which replaces as much of the bone at the proximal end of the femur as possible without invading the "safe zone" between the plug 50 and surface of the bone. Because the entire procedure can be performed percutaneously using only a local anesthetic and needle-sized opening, it is practical to perform this technique prophylactically in elderly patients or transplant recipients. If the size of the collective cavities 44, 46, 48 demand, bone cement may be applied to the interior of the cavities in layers, allowing sufficient cure time between applications.

It should be understood by an orthopedic surgeon of ordinary skill that this technique may be used for prophylactic or post-traumatic bone reinforcement according to similar techniques in the proximal humerus or distal radius.

Referring now to FIGS. 17–25, it can be seen that the device of the present invention may be employed using a similar method to facilitate intervertebral fusion to reduce or eliminate back pain associated with a diseased or damaged intervertebral disk, or as indicated for compression fractures of the spine.

Referring first to FIGS. 17–20, therein it can be seen that a substantially semi-spherical cavity 52 may be formed between adjacent vertebral bodies 54, 56. A relatively small access opening 58 may be employed to create the intervertebral cavity 52. The size of this access opening 58 is small relative to that required by prior art devices and methods and is small relative to the radius of the semi-spherical cavity 52 that can be formed. Typically, access may be obtained percutaneously at the location of an intervertebral disk 60. As described above, a guide needle or cannula 62 is inserted and maintained co-extensive with a predetermined axis X. A pilot hole is formed through the intervertebral disk tissue 60 to the desired depth, the cavitation device 10 is inserted, and, upon rotation, the angular velocity rotates the tip 14 into a perpendicular position, causing liquefication of the bone and intervertebral disk tissue in a substantially semi-spherical cavity 52. The cavitation device 10 may then be withdrawn, the liquefied material evacuated, and bone graft material injected.

Figure 21:
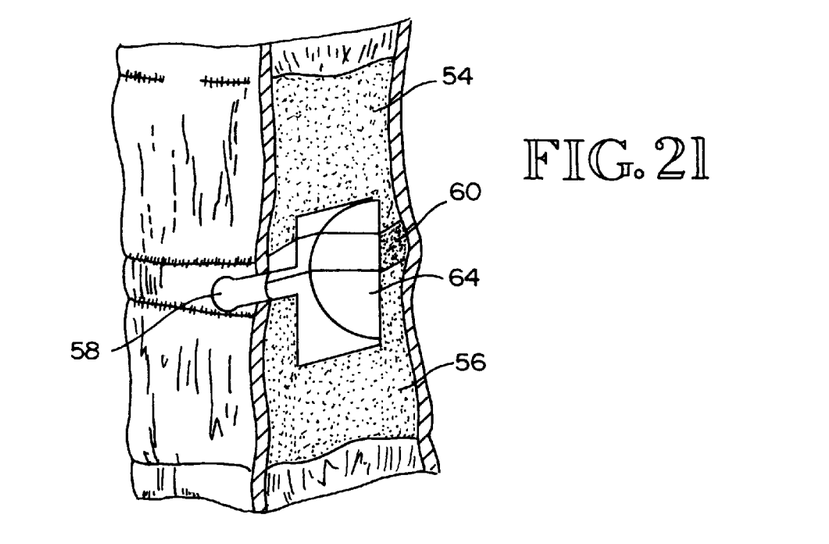
FIGS. 21–23 show views similar to those shown in FIGS. 17, 19 and 20 but in which the internal cavity is substantially cylindrical in shape.
Figure 22:
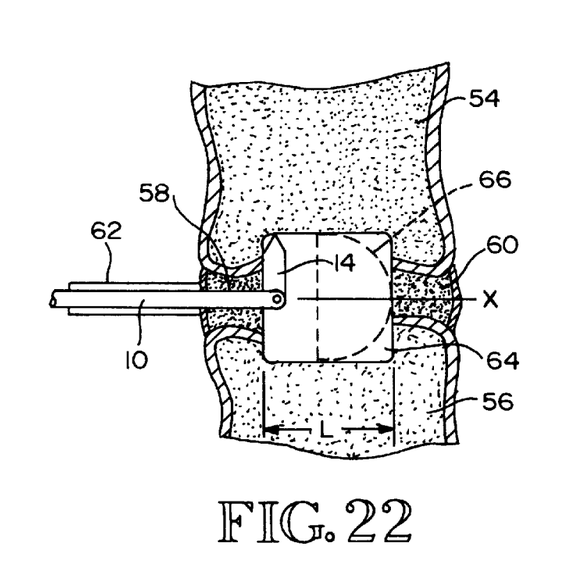
Figure 23:
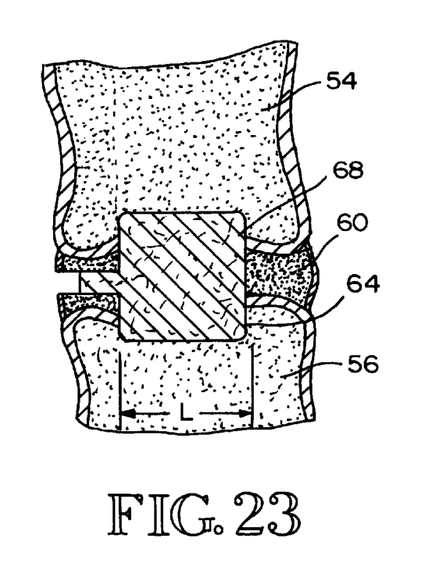

Referring now to FIGS. 21–23, therein is shown a method according to the present invention whereby the cavitation tool 10 may be used to form a substantially cylindrical cavity 64 between adjacent vertebral bodies 54, 56. The device 10 is inserted through a guide needle or cannula 62 and an entry opening 58 formed by a standard orthopedic drill. The device 10 is then rotated at a predetermined velocity, such as 80,000 rpm. Angular displacement of the tip 14 first forms a substantially semi-spherical cavity 66 (see FIG. 22). While the cavitation device 10 is still rotating, it may be moved forward and rearwardly along axis X a length L to form a substantially cylindrical cavity 64. The cavity 64 will have a length L corresponding to the axial displacement of the device 10 and a radius corresponding to the length of the cutting tip 14. Liquefied material is then evacuated as described above. Fusion material 68, such as bone cement or bone graft material, may be injected through the needle or cannula 62 into the cavity 64. One of the most useful features of this invention is the fact that the cavitation device 10 allows the entire procedure to be performed through a very small diameter (about 3 mm–5 mm) opening requiring access no greater in size than a needle or cannula.

Figure 24:
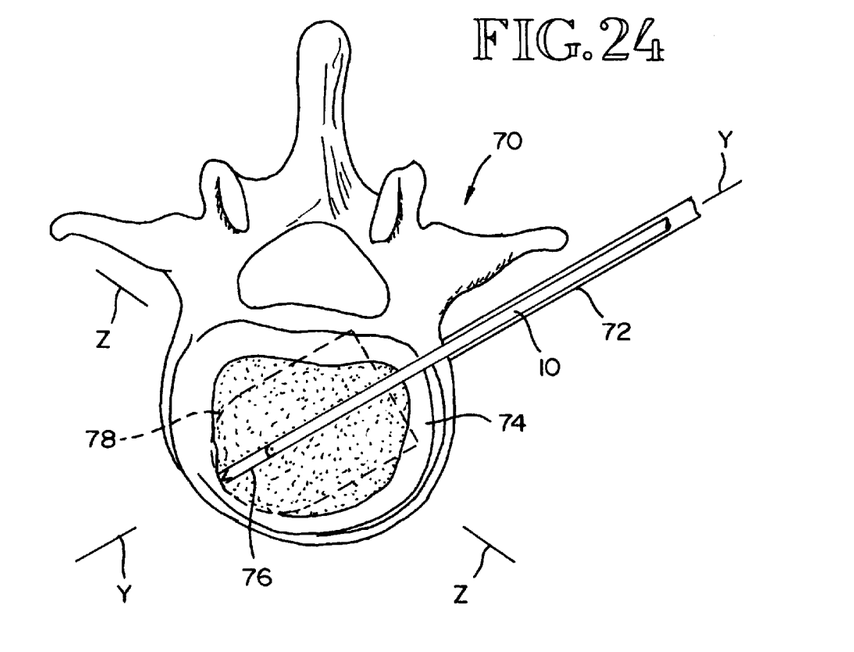
FIGS. 24 and 25 show a human third lumbar vertebra viewed from above and relative placement of intervertebral cavities formed according to a preferred method of the present invention.
Figure 25:
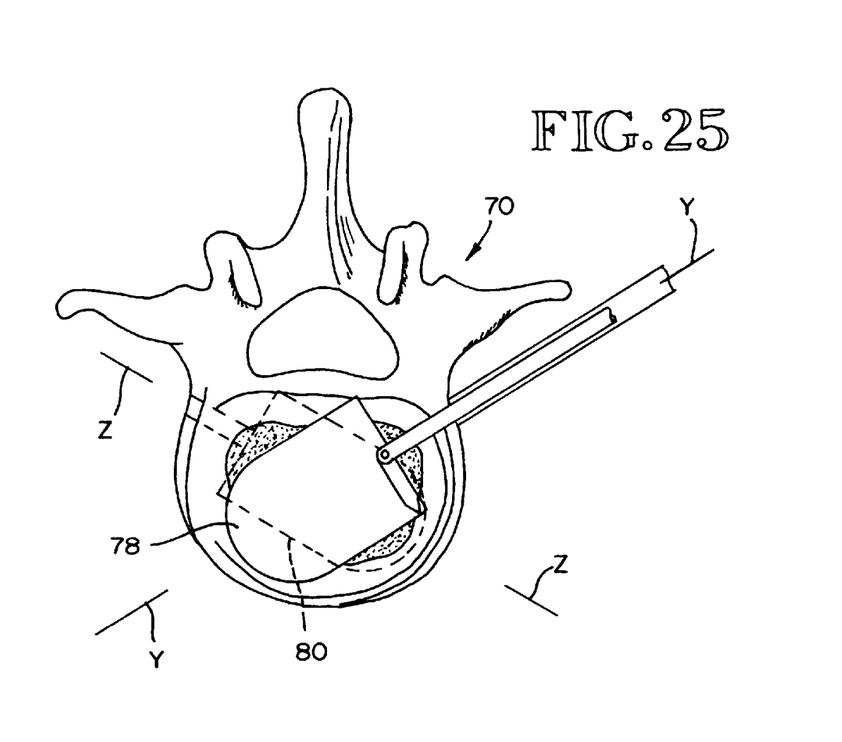

Referring to FIGS. 24 and 25, it can be seen that more than one approach may be used for forming a cavity of even greater volume in a single intervertebral space. For example, cross-axes Y, Z may be used according to the above-described technique. FIGS. 24 and 25 show, for example, the intervertebral space above the third lumbar vertebra 70. A guide cannula 72 is inserted through the soft tissue against the vertebral body 74 co-extensive with a predetermined axis, such as Y. A pilot hole 76 is formed using a standard orthopedic drill. The cavitation device 10 is inserted to a predetermined depth for the formation of the first intervertebral cavity 78. In addition to the previously-described cylindrical and semi-spherical cavity shapes, a combination or "bullet"-shaped cavity may be employed. In this case, the drill is spun to first form the semi-spherical end portion and then withdrawn a predetermined distance to form the adjoining, substantially cylindrical portion of the cavity. The cavitation device 10 is not advanced forward while spinning to form a cylindrical forward end. As illustrated in FIG. 25, a second, overlapping cavity 80 may be formed to increase the overall volume of fusion material. Bone graft or other material may be inserted through one or both percutaneous access openings.

Figure 26:
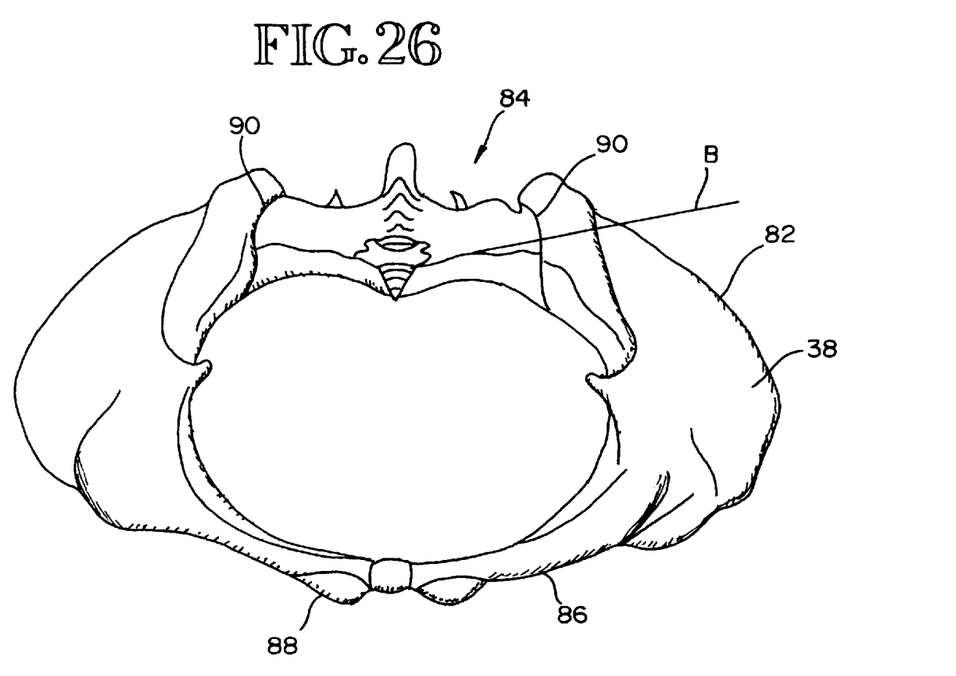
FIGS. 26 and 27 are caudal (inferior) views of a human female pelvis showing use of the present invention for sacroiliac (SI) joint fusion.
Figure 27:
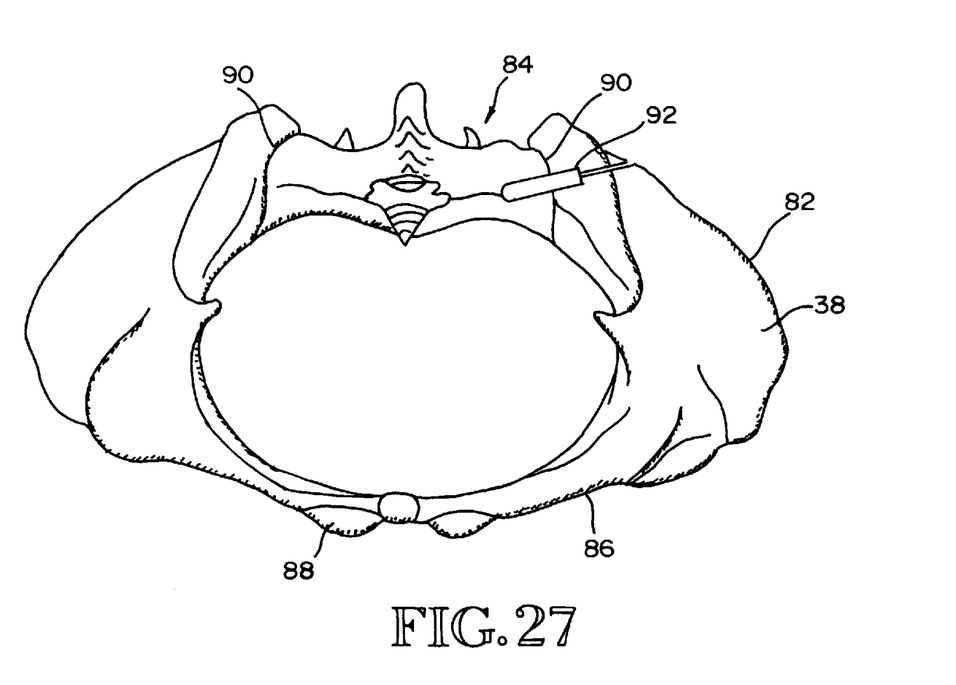

Referring now to FIGS. 26 and 27, therein is shown a caudal view of a female human pelvis 82 and sacrum 84. The pelvis is comprised of the ilium 38, the ischium 86, and pubis 88. Between the sacrum 84 and ilium 38 is an interface known as the sacroiliac (SI) joint 90. Fusion of the SI joints is sometimes indicated due to chronic pain, trauma or osteoporotic deterioration.

Inserted of a guide needle or cannula along a predetermined axis Z can be used to form a pilot hole as described above. Thereafter, a cavity 92 can be formed and filled as described above to achieve fusion between the sacrum 84 and ilium 38.

It will be understood by skilled practitioners that the cavitation device 10 of this invention may be applied to many various procedures. For example, it is not necessary that it be used to fuse joints. Instead, it may be used to remove metastatic tumors in bone or soft tissue. only a needle-sized access opening is required to facilitate ablation of a lesion in bone, soft tissue, or the brain. High speed rotation of the shaft 12 causes the hinged tip 14 to be angularly deflected resulting in virtual liquefication of tissue within the designated radius. The tissue may then be removed by irrigation and suction. If desired, the cavity may be refilled with either fusible, inert or bioabsorbable materials. These materials may also include hemostatic, antibiotic or anesthetic agents. In some case, filling the cavity may not be necessary.

It is to be understood that many variations in size, shape, and construction can be made to the illustrated and above-described embodiment without departing from the spirit and scope of the present invention. Some of the features of the preferred embodiment may be utilized without other features. Therefore, it is to be understood that the presently described and illustrated embodiment is non-limitive and is for illustration only. Instead, my patent is to be limited for this invention only by the following claim or claims interpreted according to accepted doctrines of claim interpretation, including the doctrine of equivalence and reversal of parts.

What is claimed is:

1. A percutaneous surgical cavitation device, comprising:
    an elongated shaft having a radius and an axis of rotation;
    a cutting tip having a fixed length; and
    a hinge interconnecting the shaft and cutting tip allowing free rotation of the cutting tip relative to the shaft in an arc coplanar with the shaft's axis of rotation between a first position substantially co-axial with the shaft and a second position angularly offset from the shaft's axis of rotation,
    whereby rotation of the shaft at sufficient velocity will cause the cutting tip to be deflected toward the second position to effect formation of an internal cavity having a radius greater than the radius of the shaft.

2. The device of claim 1, wherein deflection of the cutting tip is limited to an angle less than 90° from the shaft's axis of rotation.

3. The device of claim 1, wherein said second position is 90° from the shaft's axis of rotation.

4. The device of claim 1, wherein the cutting tip is hinged for movement in either of two diametrically opposite angular positions relative to the shaft's axis of rotation.

5. The device of claim 1, wherein the shaft is rotated at a velocity in excess of 30,000 rpm.

6. The device of claim 1, wherein the radius of the shaft is less than 2.5 mm.

7. The device of claim 6, wherein the cavity formed by the device has a radius greater than three times the radius of the shaft.

8. The device of claim 6, wherein the length of the cutting tip is greater than 5 mm.

9. The device of claim 6, wherein the length of the cutting tip is greater than three times the radius of the shaft.

10. A surgical method for percutaneous formation of a cavity within a body, comprising the steps of:
    a) providing a percutaneous access opening;
    b) inserting through the access opening a rotary cavitation device comprising:
        i. an elongated shaft having a radius and an axis of rotation;
        ii. a cutting tip having a fixed length; and
        iii. a hinge interconnecting the shaft and cutting tip allowing free rotation of the cutting tip in an arc coplanar with the shaft's axis of rotation between a first position substantially co-axial with the shaft and a second position angularly offset from the shaft's axis of rotation;
    c) rotating the shaft at a velocity sufficient to cause the cutting tip to be deflected from the first position toward the second position to effect formation of an internal cavity having a radius greater than the radius of the shaft; and
    d) withdrawing the device from the access opening.

11. The method of claim 10, further comprising the step of irrigation and suction to remove ablated material from the cavity.

12. The method of claim 10, further comprising the step of injecting replacement material into the cavity through the percutaneous access opening.

13. The method of claim 10, further comprising the step of axially moving the device while the shaft is being rotated.

14. The method of claim 13, wherein the shaft is advanced forwardly during rotation.

15. The method of claim 13, wherein the shaft is partially withdrawn during rotation.

16. The method of claim 10, further comprising the additional steps of:
   a) inserting a second device having a cutting tip of a second fixed length; and rotating the shaft of the second device at a velocity sufficient to cause the cutting tip to be deflected toward the second position to effect formation of a second internal cavity interconnected with the first internal cavity.

17. A method of percutaneous prophylactic replacement of osteoporotic bone, comprising the steps of:
   a) providing percutaneous access to the osteoporotic bone;
   b) drilling a guide hole along a predetermined axis to a predetermined depth;
   c) insertion of a rotary cavitation device comprising:
      i. an elongated shaft having a radius and an axis of rotation;
      ii. a cutting tip having a fixed length; and
      iii. a hinge interconnecting the shaft and cutting tip allowing free rotation of the cutting tip in an arc coplanar with the shaft's axis of rotation between a first position substantially co-axial with the shaft and a second position angularly offset from the shaft's axis of rotation;
   d) rotating the shaft at a velocity sufficient to cause the cutting tip to be deflected from the first position toward the second position to effect formation of an internal cavity having a radius greater than the radius of the shaft; and
   e) withdrawal of ablated material from the cavity through the percutaneous access; and
   f) injection of bone replacement material into the cavity through the percutaneous access.

18. The method of claim 17, wherein the bone replacement material comprises bone cement.

\* \* \* \* \*